United States Patent
Wegmann et al.

(10) Patent No.: US 6,211,413 B1
(45) Date of Patent: *Apr. 3, 2001

(54) PROCESS FOR THE PREPARATION OF PHENYL ALKYL KETONES AND BENZALDEHYDES

(75) Inventors: Arthur Wegmann, Kaisten (CH); Terry Lee Moore; Linhua Wang, both of Baton Rouge, LA (US)

(73) Assignee: Bayer Aktiengesellschaft, Leverkusen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/228,689

(22) Filed: Jan. 12, 1999

Related U.S. Application Data
(60) Provisional application No. 60/071,270, filed on Jan. 13, 1998.

(51) Int. Cl.$^7$ .................................................. C07C 49/78
(52) U.S. Cl. .......................... 568/331; 568/309; 568/323; 568/335; 568/324
(58) Field of Search ..................... 568/309, 323, 568/335, 326, 331, 626

(56) References Cited

U.S. PATENT DOCUMENTS

| | | | |
|---|---|---|---|
| 3,652,632 | 3/1972 | Vacek | 260/455 B |
| 4,537,780 | 8/1985 | Sanborn et al. | 514/464 |

FOREIGN PATENT DOCUMENTS

| | | |
|---|---|---|
| 26 04 207 | 8/1976 | (DE) . |
| WO 97/19912 | 6/1997 | (WO) . |
| WO 98/50335 | 11/1998 | (WO) . |

OTHER PUBLICATIONS

Humphlett et al, Journal of American Chemical Society, vol. 70, pp. 4020–4023, 1948.*
March, Advanced Organic Chemistry, third edition, pp. 313, 649 and 784, 1985.*
Research Disclosure, 706/Oct. 1997, No. 40221.
Research Disclosure, 348/Jun. 1996, No. 38614.
Advanced Organic Chemistry, J. March, Second Ed., 1977, p. 663.
J. Chem. Soc., 1954, pp. 1297–1302.

Derwent Abstract 98–595928 (of WO 98/50335) (1998).
Derwent Abstract 76–61958X (of DE 2604207) (1976).
* cited by examiner Primary Examiner—Sreeni Padmanabham
(74) Attorney, Agent, or Firm—Joseph C. Gil

(57) ABSTRACT

There is provided a process for the preparation of compounds of formula I

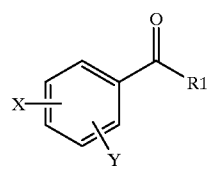

wherein:

X is H or F,

Y is $CF_3$ or F and $R_1$ is hydrogen or $C_1$–$C_2$ alkyl; in which process

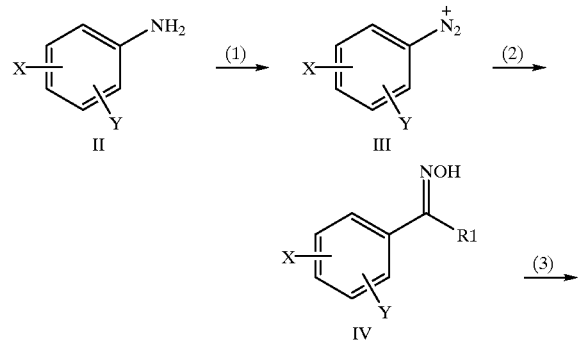

(1) a compound of formula II, wherein X and Y are as defined for formula I, is reacted with an organic or inorganic nitrite or nitrous acid;
(2) the resulting diazonium compound of formula III is reacted with an aldoxime of formula V

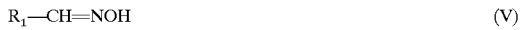

$R_1$—CH=NOH (V)

wherein $R_1$ is as defined for formula I, in presence of $CuSO_4$; and
(3) the resulting oxime of formula IV is hydrolyzed with aqueous acid to the compound of formula I.

11 Claims, No Drawings

PROCESS FOR THE PREPARATION OF PHENYL ALKYL KETONES AND BENZALDEHYDES

This application claims priority from Provisional Application Ser. No. 60/071,270 filed Jan. 13, 1998.

The invention relates to a process for the preparation of compounds of formula I

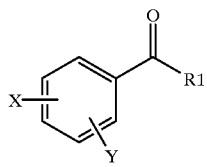

wherein:
X is H or F,
Y is $CF_3$ or F and
$R_1$ is hydrogen or $C_1$–$C_2$alkyl; in which process

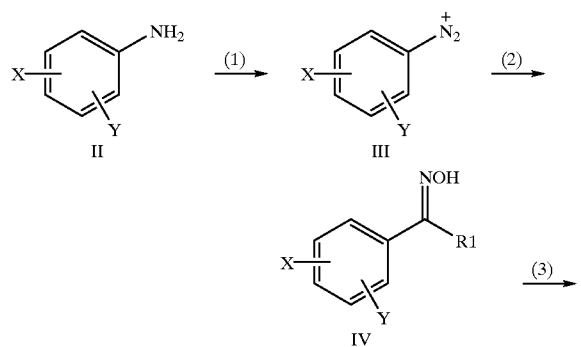

(1) a compound of formula II, wherein X and Y are as defined for formula I, is reacted with an organic or inorganic nitrite or nitrous acid;
(2) the resulting diazonium compound of formula III is reacted with an aldoxime of formula V

$R_1$—CH=NOH  (V)

wherein $R_1$ is as defined for formula I, in presence of copper powder or a copper salt; and
(3) the resulting oxime of formula IV is hydrolyzed with aqueous acid to the compound of formula I.

The compounds of formula I are important intermediates for the preparation of pharmaceuticals, dyestuffs, perfumes, pesticides and other products; e.g. WO 97/19912.

It is known that trifluoromethylphenyl alkyl ketones can be prepared from trifluoromethylphenyl halogenides and alkane carboxylic acid derivatives by Grignard reaction, for example the preparation of 3-trifluoromethyl acetophenone in Research Dislosure RD 38614, June 1996.

Furtheron, 3-trifluoromethyl acetophenone has been prepared by Grignard reaction of 3-trifluoromethylbenzonitrile, which in turn has been obtained from 3-trifluoromethyl aniline by diazotization and cyanation (J. Am. Chem. Soc. 70, p.4020,1948).

However, for an industrial process the Grignard reaction has serious disadvantages: the reaction may be difficult to start and the reaction mixture is thermally unstable which may therefore constitute a safety risk. Due to the equimolar amounts of magnesium needed, an undesirable amount of material has to be handled.

The general synthetic principle of preparing phenyl alkyl ketones and benzaldehydes by diazotization of an aniline, reaction of diazonium salts with an aldoxime and subsequent hydrolysis of the oxime is described, e.g in J. March, Advanced Organic Chemistry, 2nd Ed., p. 663, 1977; the yields are in general only 40–60%. For example, the yields of halo- and acetyl substituted acetophenones prepared by this reaction are only 30–45% (J. Chem. Soc. 1954, p.1297–1302).

The known processes for the preparation of compounds of formula I are accordingly unsatisfactory for economic, ecological and safety reasons.

It has been found that phenyl alkyl ketones and benzaldehydes of formula I can be obtained from the corresponding anilines according to this invention in yields of up to 80% and in good qualities. The method provided herewith is distinguished by ready availability of the raw materials, good technical feasibility and is economically and ecologically favorable.

DETAILED DESCRIPTION OF THE INVENTION

Reaction step (1): The diazotization reaction is carried out in an organic solvent with an organic nitrite, e.g. an alkyl nitrite as isoamyl nitrite, or an aryl nitrite, as phenyl nitrite; or, more preferably, in aqueous solution with nitrous acid or a salt thereof, in presence of an acid. Preferred nitrites are sodium nitrite, potassium nitrite, magnesium nitrite, particularly preferred is sodium nitrite. Preferred acids are hydrochloric acid, sulfuric acid and nitrosulfuric acid.

Advantageous is a temperature of −10 to +30° C. and a pH 0–3.

Reaction step (2): The diazonium compound of formula III is preferably reacted in the presence of CuCl or $CuSO_4$ at −10 to +40° C., more preferably −10 to +15° C., and at pH 2–7, more preferably at pH 3–5.

The amount of the copper salt is 1 to 20 mol %, more preferably 3 to 6 mol %, in relation to the aniline of formula II.

In a preferred mode of running the reaction step (2), an aqueous suspension of the diazonium compound of formula III and an aqueous solution of the copper salt are simultaneously added to an aqueous suspension of the aldoxime of formula V, maintaining a pH of 3–5 by simultaneously adding a base to the reaction mixture.

Reaction step (3): The phenone oxime of formula IV is hydrolyzed with aqueous acid, preferably diluted mineral acid, as hydrochloric acid, sulfuric acid, phosphoric acid, at pH <2, optionally in mixture with a solvent, wherein the product is soluble.

The temperature is not critical and may vary from 30° C. to +170° C., more preferably from 30 to 120° C.

It may be advantegeous for working up and purification of intermediates and products to run the reaction steps, in particular steps (2) and/or (3), in presence of a hydrophobic solvent, as hydrocarbons, halogenated hydrocarbons, ethers and ketones, for example hexane, cyclohexane, methylcyclohexane, benzene, toluene, xylene, mineral oil, kerosene, methylene chloride, chloroform, ethylenechloride, chlorobenzene and dichlorobenzene.

Particularly preferred is the preparation of 3-(trifluoromethyl)acetophenone and 3-(trifluoromethyl) propiophenone from 3-(trifluoromethyl)aniline according to the reaction scheme

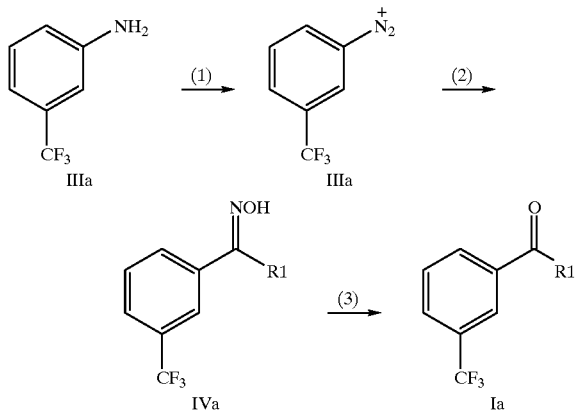

wherein $R_1$ is methyl or ethyl.

A further aspect of the invention is a process for the preparation of a compound of formula IV

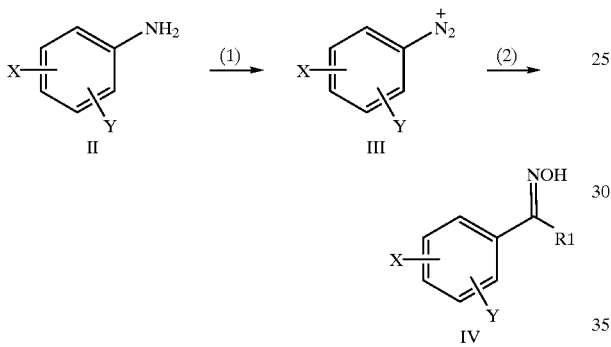

wherein:
X is H or F,
Y is $CF_3$ or F and
$R_1$ is hydrogen or $C_1$–$C_2$alkyl; in which process
(1) a compound of formula II, wherein X and Y are as defined for formula I, is reacted with an organic or inorganic nitrite or nitrous acid;
(2) the resulting diazonium compound of formula III is reacted with an aldoxime of formula V $$R_1\text{—CH=NOH} \qquad (V)$$

wherein $R_1$ is as defined for formula I, in presence of copper powder or a copper salt.

PREPARATION EXAMPLES

Example 1

Preparation of 3-(trifluoromethyl)acetophenone (1) Diazonium salt formation: To a mixture of 3-(trifluoromethyl)aniline (161 g/1.0 mol) in water (660 g) and $H_2SO_4$ (98%, 175 g/1.75 mol), an aqueous solution of $NaNO_2$ (183 g 40%/1.06 mol) is added at 0° to +5° C. over ca. 60 minutes; the mixture is stirred at 0 to +50° C. for ca. 15 minutes; the excess $NaNO_2$ is destroyed with an aqueous solution of sulfamic acid (3 g in 20 g water/0.06 mol) at 0 to +5° C.

(2) Acetophenone oxime formation: In a second reactor a mixture of acetaldoxime (71 g/1.2 mol), acetic acid (20 g), toluene (200 ml), $CuSO_4$ $5H_2O$ (3 g/0.012 mol) and water (212 g) is prepared.

To this mixture the diazonium salt (1) and $CuSO_4$ $5H_2O$ (9 g in 45 g water/0.036 mol) are added simultaneously over ca 2 hours, maintaining a temperature of −5 to 0° C. and a pH of 3 to 3.5 by adding aqueous NaOH 30% (ca. 350 g) or $NaHCO_3$ in solid form.

The reaction mixture is then stirred at ca. 25° C. for ca. 30 minures, and phases are separated.

(3) Hydrolysis: To the upper organic phase of (2), water (120 g) and concentrated HCl (37%, 180 g) are added and the mixture is stirred at ca. 90° C. (gentle reflux) for 2–3 hours. After completion of the reaction the mixture is cooled to room temperature, the phases are separated, the organic phase is optionally washed with 5% NaOH or $NaHCO_3$ solution and water, toluene is distilled off and the residue, containing the 3-(trifluoromethyl)-acetophenone, is destilled over a column at 70–75° C./1–8 mbar.

Alternatively the product may be purified by steam destillation.

Yield of 3-(trifluoromethyl)acetophenone is 75–80% (related to 3-(trifluoromethyl)aniline) with an assay of 94–99%. The unhydrolysed oxime (2–4%) may be regenerated.

Example 2

Preparation of 3-(trifluoromethyl)acetophenone

Example 1 is repeated, but CuCl (5 g, 0.05 mol) instead of $CuSO_4$ $5H_2O$ are used.

Yield of 3-(trifluoromethyl)acetophenone is 50–55% (related to 3-(trifluoromethyl)aniline).

Example 3

Preparation of 3-(trifluoromethyl)propiophenone

Example 1 is repeated, but propionaldoxime instead of acetaldoxime is used. Yield of 3-(trifluoromethyl)propiophenone is 72–77% (related to 3-(trifluoromethyl)aniline).

What is claimed is:
1. A process for the preparation of a compound of formula I

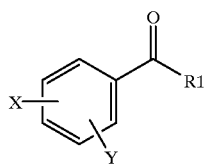

wherein:
X is H or F,
Y is $CF_3$ or F and
$R_1$ is $C_1$–$C_2$alkyl; in which process

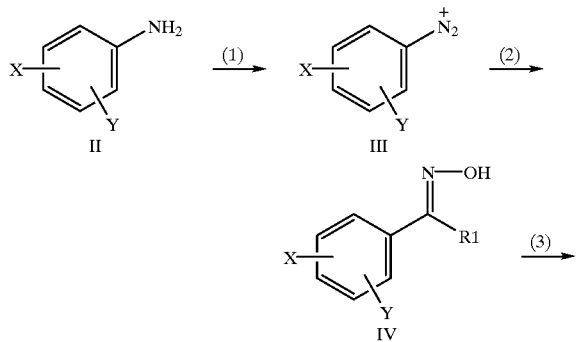

(1) a compound of formula II, wherein X and Y are as defined for formula I, is reacted with (i) an organic nitrite in an organic solvent; or (ii) nitrous acid or a salt thereof in aqueous solution, in the presence of an acid selected from the group consisting of sulfuric acid and nitrosulfuric acid;

(2) the resulting diazonium compound of formula III is reacted with an aldoxime of formula V $$R_1\text{—CH}\!\!=\!\!\text{NOH} \quad (V)$$

wherein $R_1$ is as defined for formula I, in the presence of $CuSO_4$ and a hydrophobic solvent; and (3) the resulting oxime of formula IV is hydrolyzed with aqueous acid to the compound of formula I.

2. A process according to claim 1, wherein in the reaction steps
   (1) the compound of formula II is diazotized with an alkali nitrite or with nitrous acid; and
   (3) the phenone oxime of formula IV is hydrolyzed with aqueous acid.

3. A process according to claim 1, wherein the pH in the reaction steps (1), (2) and (3) is (1) pH 0–3, (2) pH 2–7, (3) pH <2.

4. A process according to claim 1, wherein the temperature in the reaction steps (1), (2) and (3) is (1) −10 to +30° C., (2) −10 to +40° C., (3) 30 to 120° C.

5. A process according to claim 1, wherein in reaction step (2) an aqueous suspension of the diazonium compound of formula III and an aqueous solution of the $CuSO_4$ are simultaneously added to an aqueous suspension of the aldoxime of formula V.

6. A process according to claim 1, wherein in reaction step (2), the amount of the $CuSO_4$ is 1 to 20 mol %, in relation to the compound of formula II.

7. A process according to claim 1, wherein reaction step (3) is carried out in the presence of a hydrophobic solvent.

8. A process according to claim 7, wherein the hydrophobic solvent is selected from hydrocarbons, halogenated hydrocarbons, ethers and ketones.

9. A process according to claim 8, wherein the hydrophobic solvent is selected from hexane, cyclohexane, methylcyclohexane, benzene, toluene, xylene, mineral oil, kerosene, methylene chloride, chloroform, ethylenechloride, chlorobenzene and dichlorobenzene.

10. A process according to claim 1, wherein in formulae I, II, III and IV, X is H and Y is (3)—$CF_3$.

11. A process for the preparation of a compound of formula IV

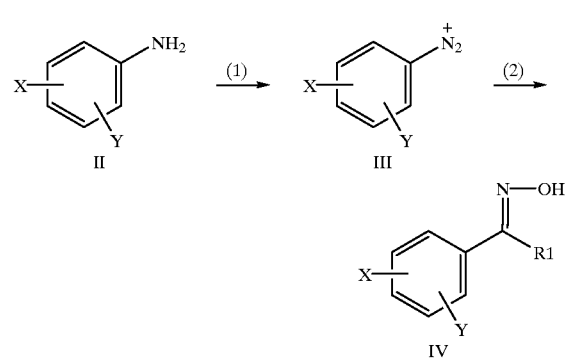

wherein:

X is H or F,

Y is $CF_3$ or F and $R_1$ is $C_1$–$C_2$alkyl; in which process (1) a compound of formula II, wherein X and Y are as defined for formula I, is reacted with (i) an organic nitrite in an organic solvent; or (ii) nitrous acid or a salt thereof in aqueous solution, in the presence of an acid selected from the group consisting of sulfuric acid and nitrosulfuric acid;

(2) the resulting diazonium compound of formula III is reacted with an aldoxime of formula V $$R_1\text{—CH}\!\!=\!\!\text{NOH} \quad (V)$$

wherein $R_1$ is as defined for formula I in claim 1, in the presence of $CuSO_4$ and a hydrophobic solvent.

* * * * *